United States Patent [19]

Buendia et al.

[11] Patent Number: 5,892,028
[45] Date of Patent: *Apr. 6, 1999

[54] 17, 20-EPOXY STEROIDS

[75] Inventors: Jean Buendia, Le Perreux Sur Marne; Rémi Chauvin, Le Pecq; Michel Vivat, Chemin de l'Autostrade, all of France

[73] Assignee: Roussel Uclaf, France

[*] Notice: This patent issued on a continued prosecution application filed under 37 CFR 1.53(d), and is subject to the twenty year patent term provisions of 35 U.S.C. 154(a)(2).

[21] Appl. No.: 946,970

[22] Filed: Oct. 8, 1997

Related U.S. Application Data

[60] Continuation of Ser. No. 557,461, Nov. 14, 1995, abandoned, which is a division of Ser. No. 401,426, Mar. 9, 1995, Pat. No. 5,504,203, which is a division of Ser. No. 182,782, Dec. 29, 1993, abandoned.

[30] Foreign Application Priority Data

Jan. 14, 1993 [FR] France ................... 93-00290

[51] Int. Cl.$^6$ .................................... C07J 21/00
[52] U.S. Cl. ..................... 540/6; 540/7; 540/46
[58] Field of Search ..................... 540/6, 7, 46

[56] References Cited

U.S. PATENT DOCUMENTS

| | | | |
|---|---|---|---|
| 2,123,217 | 7/1938 | Walls et al. | 260/131 |
| 2,813,860 | 11/1957 | Lincoln et al. | 260/239.55 |
| 3,118,882 | 1/1964 | Deghenghi | 260/239.55 |

*Primary Examiner*—Allen J. Robinson
*Assistant Examiner*—Barbara Badio
*Attorney, Agent, or Firm*—Bierman, Muserlian and Lucas

[57] ABSTRACT

A compound of the formula

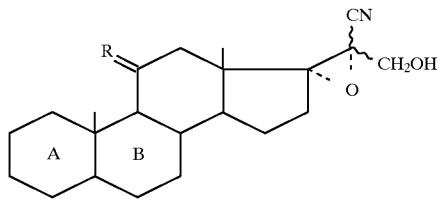

wherein R is =O or

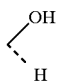

and the rings A and B are selected from the group consisting of

[steroid ring structures]

and

[steroid ring structure]

K is oxo or a protector group of oxo of the formula

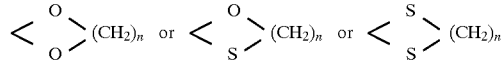

n is 2 or 3 and $R_1$ is an ether or ester remainder, K' is oxo or a protector oxime, hydrazone or semicarbazone group and the wavy lines symbolize an isomer mixture, a process for their preparation and their use as intermediates.

1 Claim, No Drawings

17, 20-EPOXY STEROIDS

PRIOR APPLICATIONS

This application is a continuation of U.S. patent application Ser. No. 557,461, filed Nov. 14, 1995, now abandoned which is a division of U.S. patent application Ser. No. 401,426 filed Mar. 9, 1995, now U.S. Pat. No. 5,504,203 which is a division of U.S. patent application Ser. No. 182,782 filed Dec. 29, 1993, now abandoned.

OBJECTS OF THE INVENTION

It is an object of the invention to provide the novel compounds of formula i and a process and intermediates for their preparation.

It is another object of the invention to provide a novel process for the preparation of the steroids of formula A.

These and other objects and advantages of the invention will become obvious from the following detailed description.

THE INVENTION

The novel 17,20-epoxy-steroids of the invention have the formula

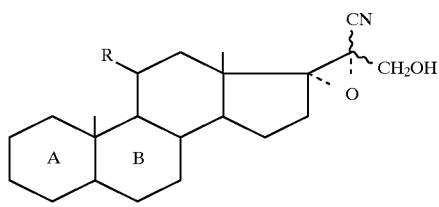

wherein R is =O or

and the rings A and B are selected from the group consisting of

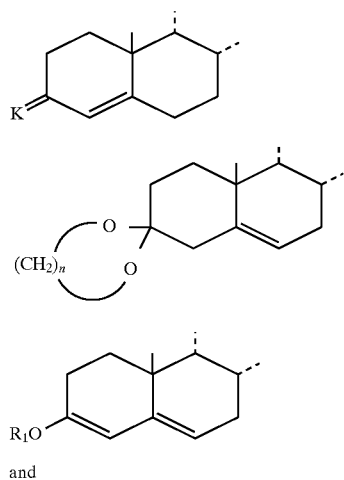

and

-continued

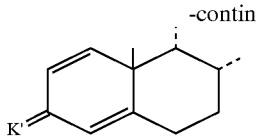

K is oxo or a protector group of oxo of the formula

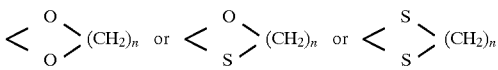

n is 2 or 3 and $R_1$ is an ether or ester remainder, K' is oxo or a protector oxime, hydrazone or semicarbazone group and the wavy lines symbolize an isomer mixture.

When $R_1$ is an ether remainder, it can be any remainder known to one skilled in the art for blocking the 3-position in this form and notably it can be alkyl or 1 to 6 carbon atoms, alkoxy-alkoxy-alkyl or 3 to 8 carbon atoms, aryl of 6 to 10 carbon atoms or aralkyl of 7 to 12 carbon atoms. When $R_1$ is alkyl, it can be methyl, ethyl, propyl, isopropyl, n-butyl, sec-butyl, tert-butyl, pentyl or hexyl. When $R_1$ is alkoxyalkoxyalkyl, it can be methoxyethoxymethyl.

When $R_1$ is aralkyl it can be benzyl or phenetyl. When $R_1$ is aryl it can be phenyl or substituted phenyl particularly by one or more alkyls. When $R_1$ is an ether remainder, it can also be a silylated group, for example trialkylsilyl such as trimethylsilyl, tert-butyldimethylsilyl or diarylalkylsilyl such as diphenyl tert-butylsilyl. When $R_1$ is an ester remainder, it can be any remainder known to one skilled in the art for blocking the 3-position in this for such as —$COR_1$, $R_1$ being an alkyl, aryl or aralkyl as defined above.

When K' is a protector group of oxime or semicarbazone type, it can be a remainder of the formula =N—OX, in which X is hydrogen, alkyl of 1 to 6 carbon atoms, preferably methyl, acyl of an organic carboxylic acid of 1 to 10 carbon atoms, preferably acetyl or benzoyl or aryl of 6 to 12 carbon atoms, or an =N—NH—CO—Y remainder, in which Y is amino or

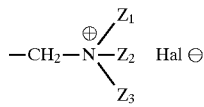

$Z_1$, $Z_2$ and $Z_3$ are alkyl of 1 to 6 carbon atoms or forming together with the nitrogen atom pyridyl and Hal is halogen, preferably chlorine or bromine.

Preferred compounds of the invention are those of the formula

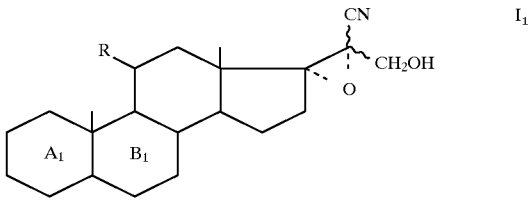

in which R has the above meaning and the rings $A_1$ and $B_1$ are selected from the group consisting of

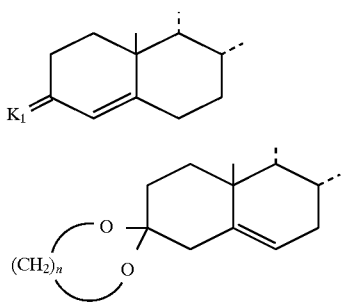

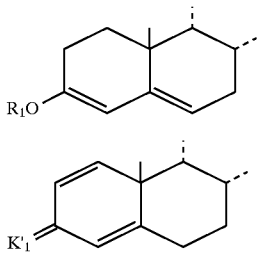

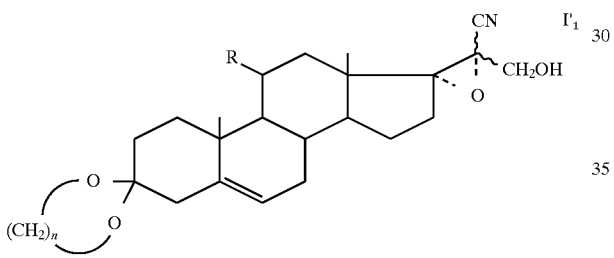

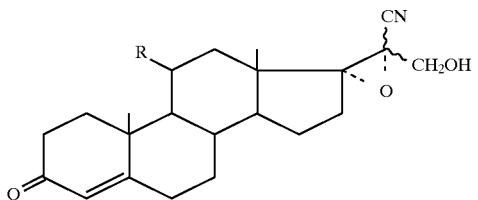

in which n and $R_1$ have the above meaning and $K_1$ and $K'_1$ are protector groups of oxo as defined above and more particularly the compounds of the formula

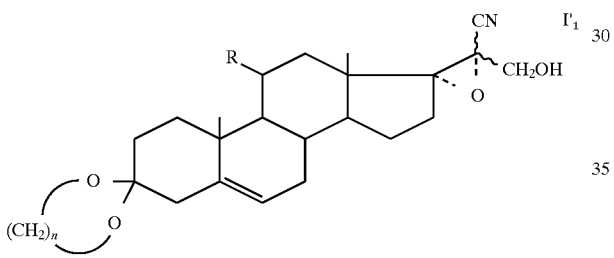

in which R and n have the above meanings. $K'_1$ is also a protector oxime, hydrazone or semicarbazone group.

More preferred are the compounds of the formula

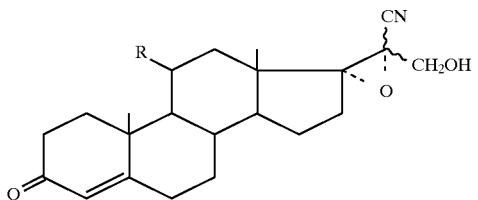

in which R has the above meaning,

The novel process of the invention for the preparation of a compound of formula I comprises protecting the 3-oxo group of a compound of the formula

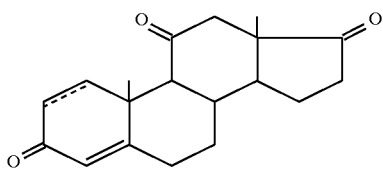

in which the dotted line is an optional double bond to obtain a compound of the formula

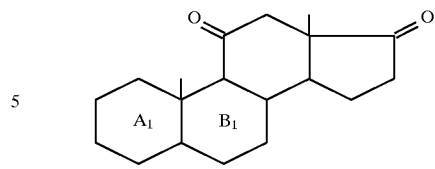

in which $A_1$ and $B_1$ are defined as above, reacting the latter with an alkyl cyanacetate of the formula $$N\equiv C-CH_2-CO_2R_2 \qquad IV$$

in which $R_2$ is alkyl or 1 to 6 carbon atoms to obtain a compound of the formula

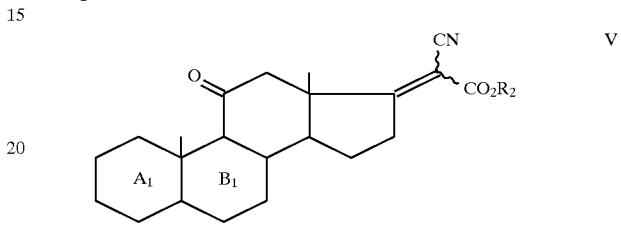

in which $R_2$, $A_1$, $B_1$ and the wavy lines are defined as above, reacting the latter with an epoxidation agent to obtain a compound of the formula

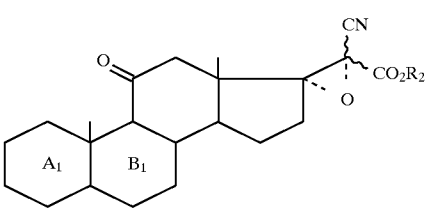

reducing the ester function of the latter to obtain a compound of the formula

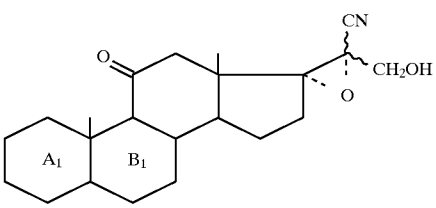

optionally reducing the 11-ketone function to obtain a compound of the formula

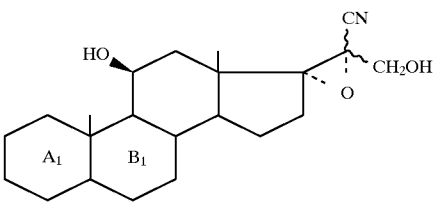

optionally releasing the 3-keto of the compounds of the formulae $I_{1B}$ and $I_{1b}$ to obtain a compound of formula $I_2$ as defined above.

The protection of the 3-ketone may be effected by methods known to one skilled in the art. Thus a diol, dithiol or a mixed thiol of the formula HO—$(CH_2)_n$—OH, HS—$(CH_2)_n$—SH or HO—$(CH_2)_n$—SH can particularly be used in an acid medium, for example in the presence of concentrated hydrochloric or hydrobromic acid in catalytic quantity, p-toluene sulfonic acid, or in the presence of a Lewis acid such as zinc chloride, titanium tetrachloride or boron trifluoride, preferably in the form of an etherate. Methylethyl dioxolane can also be used in the presence of an acid, for example one of those named above.

An alkyl, alkoxyalkoxyalkyl, aralkyl or aryl halide can also be used in the presence of a base forming the intermediate enolate, for example a hydride, an alcoholate or an alkali metal hydroxide. A trialkyl, triaryl or diarylalkylsilyl halide can also be used in an alkaline medium as above.

An appropriate acid chloride can also be used operating in the presence of a base which can be a nitrogen base such as triethylamine, pyridine, 4-dimethylamino-pyridine, or a mineral base, notably a hydride, an alcoholate or an alkali metal hydroxide. An appropriate hydroxylamine can also be used optionally in the form of the hydrochloride or another salt, or the semicarbazide or an appropriate derivative, also in the form of the hydrochloride or another salt.

The action of the alkyl cyanacetate in preferably carried out in an anhydrous medium in the presence of a primary amine such as hexylamine or a lower equivalent and a weak acid catalyst, for example a Lewis acid, an acid resin, benzoic acid or also p-toluene sulfonic acid. The operation is carried out in an organic solvent such as an aromatic solvent like benzene, toluene or xylene or cyclohexane.

The epoxidation agent is an agent which has to be inactive with respect to the nitrile group. It is preferably hydrogen peroxide used alone or in the presence of a transition metal such as titanium, tungsten or molybdenum, for example in the form of a hydrated salt. The operation is preferably carried out in a basic medium, notably in the presence of a carbonate, a bicarbonate or an alkali metal or alkaline-earth metal hydroxide in a solvent such as alkanol, preferably in a mixture with a cosolvent, notably a halogenated solvent. An alkali metal hypochlorite can also be used at a neutral pH or close to neutral. This epoxidation reaction of an α,β-ethylenic nitrile shows an original and unexpected character, insofar as the nitrile is preserved which, a priori, is not evident.

The reduction of the ester function is carried out by the action of an alkali metal borohydride by operating in an alcohol, for example sodium or lithium borohydride in ethanol. A hydride can also be used, for example lithium aluminum hydride, diethylsodium aluminum hydride, diisobutyl aluminum hydride or sodium dihydrobis(2-methoxy ethoxy) aluminate. The operation is then carried out for example in toluene or tetrahydrofuran.

The reduction of the ketone function is carried out with one of the reagents mentioned above under the solvent conditions indicated. It should be noted that the two reductions operate in an inverse order to that which is usually encountered, the reduction of the 21-ester preceding the reduction of the 11-ketone. This is also an unexpected aspect of the process. It is evident that without exceeding the scope of the invention, the two reductions can be carried out in a single operation without isolation of the intermediate 11-oxo. Such an example appears in the experimental part.

The optional release of the 3-ketone function is carried out by means appropriate to the nature of the protector group. An acid agent is used in the presence of water or a water-alkanol mixture in the case of a ketal. It can be for example a mineral or organic acid such as hydrochloric acid, hydrobromic acid, sulfuric acid, perchloric acid, nitric acid, p-toluene sulfonic acid, acetic acid, formic acid, oxalic acid or a mixture of acids, or also an acid resin, for example a sulfonic resin.

In the case of a thioketal or a mixed ketal, the deprotection of the 3-oxo function is carried out by the action of iodine in the presence of a base for example an alkali metal bicarbonate, or by the action of iodine in catalytic quantity in the presence of an oxidizing agent, particularly hydrogen peroxide, by the action of methyl iodide, glyoxylic acid, or also metal salts such as mercury or cadmium. The operation can generally be carried out in a solvent such as a lower alkanol, for example methanol or ethanol. Mixing is carried out with a halogenated solvent, for example methylene chloride in the presence of water. In the case of a mixed ketal, the deprotection is also carried out for example by a mercuric salt such as mercuric chloride in the presence of an acetic acid/potassium acetate buffer at about 100° C., by Raney nickel under the same conditions as above or by a hot hydrochloric acid-acetic acid mixture.

In the case where $R_1$ is an ether or ester remainder, an acid treatment is also used, notably under the conditions described above for the ketal. The same goes for the release of the protected ketone function in the form of the oxime or semicarbazone.

The compounds of formula I are useful intermediates for the preparation of compounds or formula A below which are described in U.S. Pat. No. 2,648,688, J. Org. Chem., Vol. 26., p. 4153–4155 and p. 5046–5052 (1961) which are useful as intermediates and/or biologically active compounds.

The process for the preparation of a compound of the formula

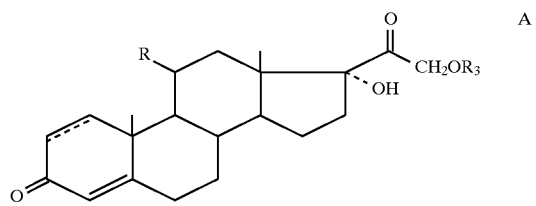

wherein R is defined as above, $R_3$ is a hydroxy protector group and the dotted line is an optional second carbon-carbon bond comprises protecting the 21-hydroxy function of a compound of formula I to obtain a compound of the formula

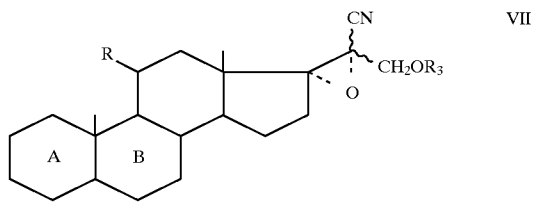

wherein R, $R_3$, and A and B have the above definitions, hydrating the nitrile function to obtain a compound of the formula

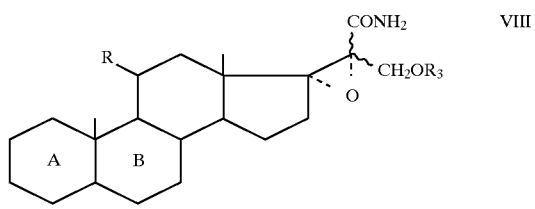

subjecting the latter to a Hofmann degradation reaction to obtain a compound of the formula

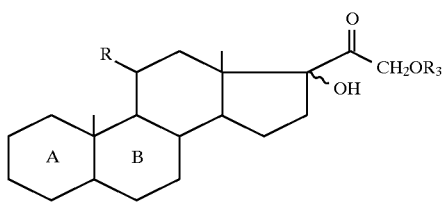

optionally releasing the 3-ketone function to obtain the expected compound of formula A.

By protector group of the hydroxy is meant a group which is stable under the conditions or the process and more particularly of the Hofmann degradation, that is to say essentially an ether remainder and especially an alkyl of 1 to 6 carbon atoms, preferably methyl, ethyl or propyl.

Such ethers are prepared notably by the action of a corresponding halide in the presence of a basic agent such as by the action of an appropriate iodide or bromide in the presence of a strong base such as a hydride, an amide or an alkali metal alcoholate. The operation is carried out in a solvent which can be preferably an ether such as tetrahydrofuran or dioxane, dimethylformamide or dimethylsulfoxide.

The hydration of the nitrile function is carried out by the action of an aqueous mineral base, especially by the action of an alkali metal hydroxide such as sodium, potassium or lithium hydroxide. The operation is carried out in the presence of a preferably polar organic solvent such as tetrahydrofuran, dioxane, dimethylformamide, dimethylsulfoxide or acetonitrile.

The degradation of the amide is carried out by the action of an alkali metal or alkaline-earth metal hypohalite, particularly sodium hypochlorite or hypobromite, if appropriate formed in situ. The operation is carried out in a solvent which is preferably one of those mentioned above and in the presence of water.

The degradation is carried out without intermediately isolating the amide of formula VIII. The optional release of the ketone function is carried our under the conditions specified above.

Novel intermediates are compounds of the formula:

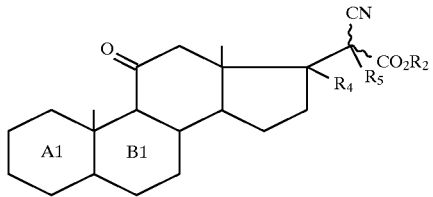

wherein $A_1$, $B_1$, $R_2$ and the wavy lines are defined as above and $R_4$ and $R_5$ form together a carbon-carbon bond or an α-epoxy; compounds of the formula

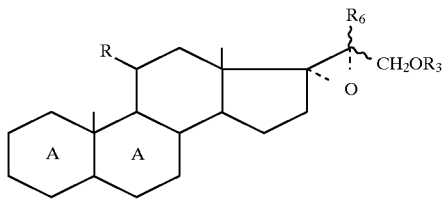

wherein A, B, R or $R_3$ and the wavy lines are defined as above and $R_6$ is cyano or carbamoyl and the compounds of the formula:

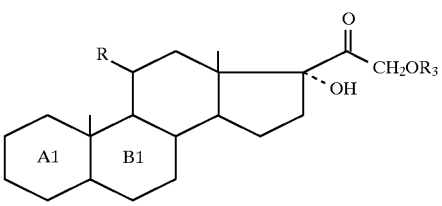

wherein $A_1$, $B_1$, $R_3$ and R are defined as above.

The compound of formula II is described in the U.S. Pat. No. 2,344,600.

In the following examples, there are described several preferred embodiments to illustrate the invention. However, it should be understood that the invention is not intended to be limited to the specific embodiments.

EXAMPLE 1 cyclic 3,3-(1,2-ethanediyl)-acetal 17,20-epoxy-20-cyano-$\Delta^5$-pregnene-21-ol-3,11-dione Stage A: cyclic 3,3-(1,2-ethanediyl)-acetal$\Delta^5$-androstene-3,11,17-trione 10 g of adrenosterone and 150 ml of methylethyldioxolane were mixed together under an inert gas atmosphere and the mixture was refluxed for 30 minutes. 0.033 g of p-toluene sulfonic acid were added and reflux was continued for 6 hours 30 minutes. The reaction medium was cooled to 50° C. and 0.5 ml of triethylamine were added, followed by concentration to dryness under reduced pressure. The product was crystallized from ethanol, separated out and washed with cold ethanol, then with an ethanol-water mixture and dried to obtain 6.35 g of the expected product melting at 196°–198° C.

IR Spectrum (CHCl$_3$) Absorption at 1740 cm$^{-1}$ (17 C=O) and 1706 cm$^{-1}$ (11=O).

NMR Spectrum (CDCl$_3$, 250 MHz, ppm) 0.86: 18-CH$_3$; 3.95: CH$_2$ of the ketal; 5.38: H in position 6.

Stage B: ethyl 20-cyano 3,3-(1,2-ethanediyl bisoxy) 11-oxo-$\Delta^5$, 17(20)-pregna-dien-21-oate 6.25 g of the product or Stage A, 100 ml of xylene, 6.2 ml of ethyl cyanacetate, 3.1 ml of hexylamine and 0.31 g of benzoic acid were mixed together and the mixture was refluxed for 24 hours while eliminating the water formed during the reaction, then cooled to 15° C. 5 ml of a 10% aqueous sodium bicarbonate solution were added and the mixture was stirred for one hour, followed by decanting. The organic phase was washed with water and concentrated under reduced pressure to obtain a crystallized product which was crystallized from ethyl acetate. After washing the crystals with hexane and drying, 3.42 g of the expected product were obtained. By chromatographing the mother liquors on silica and eluting with a cyclohexane-toluene-ethyl acetate mixture (2/2/1), 2.75 g of additional expected product were obtained.

IR Spectrum (CHCl$_3$) Absorptions at 2226 cm$^{-1}$ (C≡N), 1725–1707 cm$^{-1}$ (C=O and conjugated ester), 1511 cm$^{-1}$ (C=C).

NMR Spectrum (CDCl$_3$, 300 MHz, ppm) 1.01: CH$_3$ in position 18; 1.23: CH$_3$ in position 19; 1.34 (t): CH$_3$ of the ester; 3.94: CH$_2$ of the acetal, 4.27 (q): CH$_2$ of the ester; 5.36: H in position 6.

Stage C: ethyl 20-cyano-3,3-(1,2-ethanediyl-bis-oxy)-17,20-epoxy-$\Delta^5$-pregnene-11-one-21-oate 0.255 g of the product of Stage B, 1 ml of methylene chloride and 4 ml of ethanol were mixed together under an inert gas atmosphere and 0.2 ml or 30% hydrogen peroxide were added to the solution at 20° C. A saturated solution of potassium bicarbonate in ethanol at 50% was added until pH of 9 was obtained and then the medium was stirred at a constant pH for 3 hours 30 minutes. Next, 0.5 ml of 10% acetic acid were added, followed by concentration to dryness under reduced pressure at about 25° C. The residue was taken up in a mixture or water and methylene chloride and decanting was carried out. The organic phase was concentrated to dryness and the residue was chromatographed on silica, eluting with a methylene chloride-ethyl acetate mixture (95-5) to obtain 0.236 g of the expected product.

IR Spectrum (CHCl$_3$) Absorption at 1764 cm$^{-1}$ and 1740 cm$^{-1}$: carbonyl; 1707 cm$^{-1}$: 11-keto; 2243–2235 cm$^{-1}$: non-conjugated C≡N; 1672 cm$^{-1}$: C=C.

NMR Spectrum (CDCl$_3$, 300 MHz, ppm) 1.05 (s) (3H): 18-CH$_3$; 1.22 (s) (3H): 19-CH$_3$; 3.95 (m) (4H): ketal; 5.30 (m) (1H): H in position 6; 1.37 (3H); 4.35 (2H): —CH$_2$—CH$_3$—.

Stage D: cyclic 3,3-(1,2-ethanediyl)-acetal 17,20-epoxy-20-cyano-Δ$^5$-pregnene-21-ol-3,11-dione 4.36 g of the product of Stage C, 44 ml of toluene and 44 ml of ethanol were mixed together under an inert gas atmosphere and 0.195 g of sodium borohydride were added to the solution. The mixture was stirred for 2 hours at 20° C. and then cooled to 0° C. 0.097 g of sodium borohydride were added and the mixture was stirred for 2 hours at 0° C. Then, 5 ml of 20% ammonium chloride were added and the mixture was stirred for 30 minutes at 10° C., followed by concentration to half the volume. 50 ml of water and 50 ml of ethyl acetate were added and the mixture was stirred, then decanted. The organic phase was dried and concentrated to dryness. The residue was chromatographed on silica eluting with a methylene chloride-ethyl acetate mixture (8-2) to obtain 3.17 g of the expected product.

IR Spectrum (CHCl$_3$) Absorptions at 3605 cm$^{-1}$ (—OH), 2242 cm$^{-1}$ (—C≡N), 1705 cm$^{-1}$ (C=O), 1670 cm$^{-1}$ (C=C).

NMR Spectrum (CDCl$_3$, 200 MHz, ppm) 1.01: CH$_3$ in position 18; 1.22: CH$_3$ in position 19; 3.81: CH$_2$ in position 21; 3.95: CH$_2$ of the acetal; 5.35: H in position 6.

EXAMPLE 2 cyclic 3,3-(1,2-ethanediyl)-acetal-17,20-epoxy-20-cyano-Δ$^5$-pregnene-11β,21-diol-3-one 5.9 g of the product of Stage C of Example 1, 120 ml of ethanol and 1.2 g of sodium borohydride were mixed together under an inert gas atmosphere and then the mixture was stirred for 45 minutes at ambient temperature. The mixture was heated to 45° C. and after 90 minutes, a further 0.6 g of sodium borohydride were added, then again after 3 hours. After 4 hours 30 minutes, the mixture was cooled to 0° to 5° C. and 200 ml of a saturated solution of ammonium chloride were added slowly while keeping the reaction temperature below 15° C. After stirring, a water-ethyl acetate mixture was introduced, followed by decanting. The organic phase was dried and concentrated to dryness. The residue was purified by chromatography on silica and eluting with a cyclohexane-ethyl acetate mixture (1-1) to obtain 3 g of the expected product.

IR Spectrum (CHCl$_3$) Absorptions at 3614 cm$^{-1}$ (OH) 2240 cm$^{-1}$ (—C≡N), absence of C=O.

NMR Spectrum (CDCl$_3$, 200 MHz; ppm) 1.28 (s): CH$_3$ in position 18; 1.32 (s); CH$_3$ in position 19; 3.76 and 3.87 (d–J=12): CH$_2$ in position 21; 3.95: CH$_2$ of the ketal; 4.5: H in position 11; 5.25: H in position 6.

EXAMPLE 3

21-methoxy-Δ$^4$-pregnene-17α-ol-3,11,20-trione

Stage A: cyclic 3,3-(1,2-ethanediyl)-acetal 17,20-epoxy-20-cyano-21-methoxy-Δ$^5$-pregnene-3,11-dione 20 ml of anhydrous tetrahydrofuran and 0.668 g of sodium hydride at 50% in oil were mixed together under an inert gas atmosphere and a solution of 4.21 of the product of Example 1 in 30 ml of tetrahydrofuran were added over 5 minutes with stirring at 20°–22° C. The mixture was stirred for 40 minutes at 20°/22° C., then after 3 ml of methyl iodide were added, the mixture was stirred for one hour. The solution was poured into a mixture of 50 ml of a 20% aqueous solution of ammonium chloride and 50 g of ice. Extraction was carried out with ethyl acetate and the organic phase was dried and concentrated to dryness to obtain 4.61 g of crude product which was purified by impasting in an isopropyl either-ethyl acetate mixture. After drying, 4.03 g of the expected product were obtained melting at approximately 256° C.

IR Spectrum (CHCl$_3$) Absorptions at 2248 cm$^{-1}$ (—C≡N) 1706 cm$^{-1}$ (C=O), 1670–1637 cm$^{-1}$ (C—C), absence of OH.

NMR Spectrum (CDCl$_3$, 300 MHz, ppm) 1.00 (s): CH$_3$ in position 18; 1.22 (s): CH$_3$ in position 19; 3.47 (s): O—CH$_3$; 3.57: —CH$_2$ in position 21; 3.95: CH$_2$ of the ketal; 5.35: H in position 6.

Stage B: cyclic-3,3-(1,2,-ethanediyl)-acetal 17,20-epoxy-20-carbamoyl-21-methoxy-Δ$^5$-pregnene-3,11-dione- 0.36 g of the product of Stage A and 0.049 g of lithium hydroxide were dissolved in 7.5 ml of dioxane and 2.5 ml of water and the solution was refluxed for 2 hours. The mixture was cooled to ambient temperature, then diluted with 0.2N hydrochloric acid. Extraction was carried out with methylene chloride and the organic phase was dried and concentrated to dryness to obtain 0.378 g of the expected product which was used as is in the following stage.

NMR Spectrum (CDCl$_3$, 200 MHz, ppm) 0.88 (s): CH$_3$ in position 18; 1.17 (s): CH$_3$ in position 19; 3.24 (1H, d, J=11 Hz) and 4.18 (1H, d, J=11 Hz): CH$_2$ in position 21; 3.39 (3H, s): O—CH$_3$; 5.37 (1H, dd J=2.5 Hz and J=7.5 Hz): H in position 6; 5.67 (1H, d, J=4 Hz) and 6.19 (1H, d, J=4 Hz): —NH$_2$—.

Stage C: cyclic 3,3-1,2-ethanediyl)-acetal-21-methoxy-Δ$^5$-prenene-17α-ol-3,11,20-trione 0.36 g of the product of Stage A and 0.049 g of lithium hydroxide were mixed together under an inert gas atmosphere and 5 ml of dioxane and 1 ml of water were added. The mixture was refluxed for 3 hours and the solution was cooled with an ice bath. Then, 0.5 ml of 15% sodium hypochlorite were added and the mixture was stirred for 3 hours at 0°/+20° C. while adding a further 1 ml of 15% sodium hypochlorite twice. The reaction mixture was diluted with water and extracted with ether. The organic phase was dried and concentrated to dryness. The residue was chromatographed on silica, eluting with an ethyl acetate-cyclohexane mixture (15-85, then 50-50) to obtain 0.073 g of the expected product which was crystallized from a methylene chloride-hexane mixture to obtain the product melting at 236° C.

IR Spectrum (CHCl$_3$) Absorptions at 3610 cm$^{-1}$: CH, 1703 cm$^{-1}$ and 1670 cm$^{-1}$: C=O and C=C.

NMR Spectrum (CDCl$_3$, 200 MHz, ppm) 0.63 (s, 3H): CH$_3$ in position 18; 1.21 (s, 3H): CH$_3$ in position 19; 3.45 (s, 3H): OCH$_3$; 3.95 (4H): —CH$_2$ of the acetal, 4.17 (d, J=18 Hz, 1H) and 4.36 (d, J=18 Hz, 1H): CH$_2$ in position 21, 5.36 (m, 1H): H in position 6.

Stage D: 21-methoxy-$\Delta^4$-pregnene-17$\alpha$-ol-3,11,20-trione 0.036 g of the product of Stage C were mixed with 1 ml of methanol and 0.2 ml of 2N hydrochloric acid and the mixture was stirred for 4 hours. The precipitate was separated out and dried to obtain 0.012 g of the expected product. By concentration of the mother liquors, more of the desired product was obtained.
IR Spectrum (CHCl$_3$) Absorptions at 3610–3480 cm$^{-1}$: 17-OH, 1706 cm$^{-1}$ 11 C=O and 20 C=O; 1667 cm$^{-1}$; conjugated 3-C=O; 1617 cm$^{-1}$ $\Delta$ 4,5.
NMR Spectrum (CDCl$_3$, 200 MHz, ppm) 0.67 (s): CH$_3$ in position 18; 1.41 (s): CH$_3$ in position 19; 3.44 (s): O—CH$_3$; 3.47 (s): OH in position 17; 4.19 (d) and 4.31 (d): CH$_2$ in position 21, 5.74: H in position 4.

EXAMPLE 4

21-methoxy-$\Delta^4$-pregnene-17$\alpha$-ol-3,11,20-trione

Stage A: 17,20-epoxy-20-cyano-$\Delta^4$-pregnene-21-ol-3,11-dione 4.1 g of the product of Example 1, 80 ml of methanol and 7 ml of methylene chloride were mixed together under an inert gas atmosphere and 20 ml of 2N hydrochloric acid were added. The mixture was stirred at ambient temperature for 4 hours and the crystals formed were separated out, flashed with a methanol-water mixture (8-2), then with water. By concentration of the mother liquors, more of the product was isolated. After drying, the product was purified by chromatography on silica eluting with a chloroform-isopropanol mixture (95-5) to obtain 3.3 g of the expected product melting at 256° C.
IR Spectrum (CHCl$_3$) Absorptions at 3310 cm$^{-1}$: OH, 1703 and 1654 cm$^{-1}$: C=O; 1612 cm$^{-1}$: C=C.
NMR Spectrum (CDCl$_3$, 300 MHz, ppm) 1.04 (s): CH$_3$ in position 18; 1.42 (s): CH$_3$ in position 19; 3.84 (AB syst): —CH$_2$OH; 5.74 (s): H in position 4.
Analysis: C$_{22}$H$_{27}$O$_4$N (369.52)

|  | C % | H % | N % |
| --- | --- | --- | --- |
| Calculated: | 71.4 | 7.3 | 3.8 |
| Found: | 71.3 | 7.3 | 3.5 |

Stage B: 17,20-epoxy-20-cyano-21-methoxy-$\Delta^4$-pregnene-3,11-dione

The ether in position 21 was prepared by the process of Stage A of Example 3, starting with the product obtained in Stage A above.

Stage C: 21-methoxy-$\Delta^4$-pregnene-17$\alpha$-ol-3,11,20-trione

Using the procedure of Stage B of Example 3, the product of Stage B was reacted with intermediate isolation of 17,20-epoxy-20-carbamoyl-21-methoxy-$\Delta^4$-pregnene-3,11-dione, then by treating this compound with Javel water according to the Hofmann degradation principle as indicated in Stage C of Example 3, by carrying out this degradation without intermediately isolating the 20-carbamoyl compound. The expected product was obtained, identical to that obtained in Stage D of Example 3.

EXAMPLE 5

21-methoxy-$\Delta^4$-pregnene-11$\beta$,17$\alpha$-diol-3,20-dione

Stage A: cyclic 3,3-(1,2-ethanediyl)-acetal-17,20-epoxy-20-cyano-21-methoxy-$\Delta^5$-pregnene-11$\beta$-ol-3-one Using the procedure of Stage A of Example 3, the product of Example 2 was reacted to obtain the desired product.

Stage B: cyclic 3,3-(1,2-ethanediyl)-acetal-21-methoxy-$\Delta^5$-pregnene-11$\beta$,17$\alpha$-diol-3,20-dione Using the procedure of Stage B of Example 3, the product of Stage A was reacted with intermediate isolation of 17,20-epoxy-20-carbamoyl-21-methoxy-$\Delta^5$-pregnene-11$\beta$-ol-3-one cyclic 3,3-(1,2-ethanediyl) acetal. Then by treating this compound with Javel water according to the Hofmann degradation as indicated in Stage C of Example 3, by carrying out this degradation without intermediately isolating the 20-carbamoyl compound, the desired product was obtained.

Stage C: 21-methoxy-$\Delta^4$-pregnene-11$\beta$,17$\alpha$-diol-3,20-dione

Using the procedure of Stage D of Example 3, the compound of Stage B was reacted to obtain the expected product.

EXAMPLE 6

21-methoxy-$\Delta^4$-pregnene 17$\beta$, 17$\alpha$-diol-3,20-dione

Stage A: 17,20-epoxy-20-cyano-$\Delta^4$-pregnene-11$\beta$21-diol-3,20-dione 3 g of the product of Example 2, 66 ml of methanol and 10 ml of methylene chloride were mixed together under an inert gas atmosphere and 15 ml of 2N hydrochloric acid were added. The mixture was stirred at ambient temperature for 2 hours and the crystals were separated out and flashed with a methanol-water mixture 75-25), then with water. The crystals which have precipitated from the mother liquors were separated out and washed with water, finally, the mother liquors were concentrated and the crystals formed were separated out and washed with water. All the crystals were dried and crystallized from methanol to obtain 1 g of the expected product.
IR Spectrum (CHCl$_3$) Absorptions at 3485 cm$^{-1}$: OH/NH region, 2240 cm$^{-1}$: C≡N, 1628 and 1610 cm$^{-1}$: conjugated C—O.
NMR Spectrum (CDCl$_3$, 300 MHz, ppm) 1.34 (s): CH$_3$ in position 18; 1.50 (s): CH$_3$ in position 19; 3.81 (d): OH in position 11; 3.76 and 3.88 (AB syst): CH$_2$ in position 21;

4.45: H in position 11; 5.69 (s): H in position 4; 7.18: mobile H.

Analysis: $C_{22}H_{29}O_4N$ (371.52)

|  | C % | H % | N % |
|---|---|---|---|
| Calculated: | 71.12 | 7.86 | 3.77 |
| Found: | 71.00 | 7.00 | 3.70 |

Stage B: 17,20-epoxy-20-cyano-21-methoxy-$\Delta^4$-pregnene-11β-ol-3-one

The ether in position 21 was prepared by the process of Stage A of Example 3, the product of Stage A was reacted to obtain the desired product.

Stage C: 21-methoxy-$\Delta^4$-pregnene-11β,17α-diol-3, 20-dione

Using the procedure or Step B of Example 3, the product of Stage B was reacted with intermediate isolation of 17,20-epoxy-20-carbamoyl-21-methoxy-$\Delta^4$-pregnene-11β-ol-3-one. Then by treating this compound with Javel water according to the Hofmann degradation by carrying out this degradation without intermediately isolating the 20-carbamoyl product, the expected product was obtained, identical to that of Stage C of Example 5.

Various modifications of the compounds and process of the invention may be made without departing from the spirit and scope thereof and it is to be understood that the invention is intended to be limited only as defined in the appended claims.

What is claimed is:

1. A compound having a formula selected from

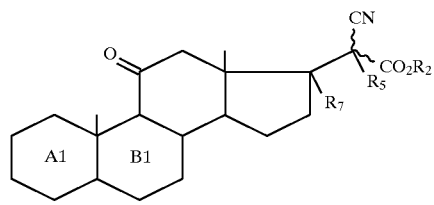

and

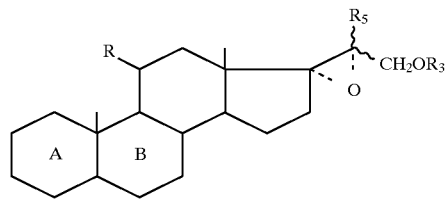

wherein rings A and B are selected from the group consisting of

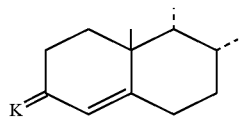

-continued

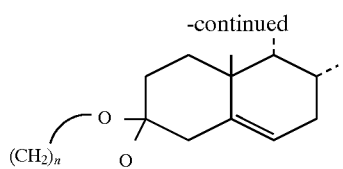

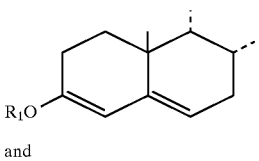

and

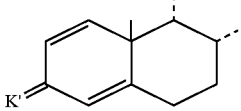

rings $A_1$ and $B_1$ are selected from the group consisting of

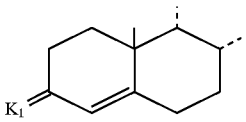

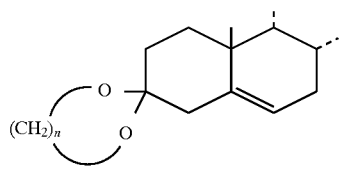

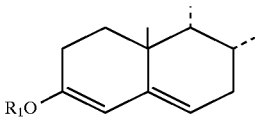

and

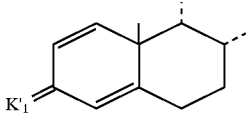

$R_2$ is alkyl of 1 to 6 carbon atoms, the wavy lines indicate an isomer mixture, $R_4$ and $R_5$ together form an α-epoxy, $R_3$ is a hydroxy protective group, $R_6$ is —CN or carbamoyl, R is =O or

K is selected from the group consisting of oxo,

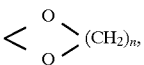

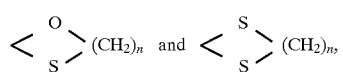
n is 2 or 3, K' is selected from the group consisting of oxo, oxime, hydrazone and semicarbazone, $K_1$ is selected from the group consisting of
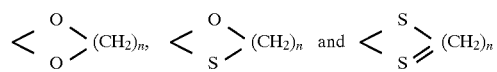
and n is 2 or 3 and $K'_1$ is a protective group selected from the group consisting of oxime, hydrazone and semicarbazone and $R_1$ is an ether or ester function.
* * * * *